United States Patent
Pedrazzini (10) Patent No.: US 8,267,451 B2
(45) Date of Patent: Sep. 18, 2012

(54) CONTAINER GRIPPER PROVIDED WITH A POSITION SENSOR

(75) Inventor: Gianandrea Pedrazzini, Paradiso (CH)

(73) Assignee: INPECO IP, Ltd., Valletta (MT)

( * ) Notice: Subject to any disclaimer, the term of this patent is extended or adjusted under 35 U.S.C. 154(b) by 316 days.

(21) Appl. No.: 12/517,500

(22) PCT Filed: Dec. 4, 2006

(86) PCT No.: PCT/EP2006/069283
§ 371 (c)(1), (2), (4) Date: Jul. 27, 2009

(87) PCT Pub. No.: WO2008/067846
PCT Pub. Date: Jun. 12, 2008

(65) Prior Publication Data
US 2010/0066109 A1 Mar. 18, 2010

(51) Int. Cl.
*B25J 13/08* (2006.01)
*B25J 15/10* (2006.01)
(52) U.S. Cl. .............. 294/207; 294/119.1; 294/907
(58) Field of Classification Search ............ 294/192, 294/203, 207, 119.1, 907; 901/37, 46, 47; 269/32, 34
See application file for complete search history.

(56) References Cited

U.S. PATENT DOCUMENTS

| | | | |
|---|---|---|---|
| 4,730,861 A | 3/1988 | Spencer | |
| 4,809,191 A | 2/1989 | Domeier et al. | |
| 5,125,708 A * | 6/1992 | Borcea et al. | 294/207 |
| 5,945,798 A | 8/1999 | Stagnitto et al. | |
| 5,967,581 A * | 10/1999 | Bertini | 294/207 |
| 6,123,375 A * | 9/2000 | Fussey et al. | 294/207 |
| 6,264,419 B1 * | 7/2001 | Schinzel | 414/751.1 |
| 6,386,609 B1 * | 5/2002 | Govzman | 294/207 |
| 6,827,381 B1 * | 12/2004 | Reichert et al. | 294/207 |
| 6,830,273 B2 * | 12/2004 | Michler et al. | 294/207 |
| 7,562,923 B2 * | 7/2009 | Han et al. | 294/119.1 |
| 2004/0074320 A1 | 4/2004 | Itoh | |

* cited by examiner

*Primary Examiner* — Dean Kramer
(74) *Attorney, Agent, or Firm* — Birch, Stewart, Kolasch & Birch, LLP (57) ABSTRACT

Container gripper comprising a main frame (2) and movable supporting members (7) for gripper fingers (8-9) movable between an open position and a closed position. The container gripper is provided with a finger displacement detecting sensor (20, 21) which is responsive to the instantaneous position of the gripper fingers (8, 9). The finger detecting sensor may consist of a Hall effect assembly (20) formed by a magnet (10) and a Hall effect sensor (4) or of an optical encoder (21).

6 Claims, 8 Drawing Sheets

CONTAINER GRIPPER PROVIDED WITH A POSITION SENSOR

The present invention concerns a container gripper provided with a position sensor.

As used herein, the term "container" means an article that contains a biological specimen and has a tubular opening for access of the contents, e.g., a test tube.

In an automated clinical chemistry laboratory it is often necessary to handle a specimen container by a gripper.

A control unit has to check if the gripper has grasped the container or not and also to detect the transversal size of the container.

Object of the present invention is to provide a container gripper which is able to feed the control unit with an electric signal indicative of the position of the container gripper.

According to the invention said object is achieved by a container gripper comprising a main frame and movable supporting members for gripper fingers movable between an open position and a closed position, characterized in that it comprises a finger displacement sensor which is responsive to the instantaneous position of the gripper fingers.

The detecting sensor may be, for instance, an optical encoder or a Hall effect sensor.

The characteristics and advantages of the present invention will appear evident from the following detailed description of embodiments thereof illustrated as non-limiting examples in the enclosed drawings, in which.

Figure 1:
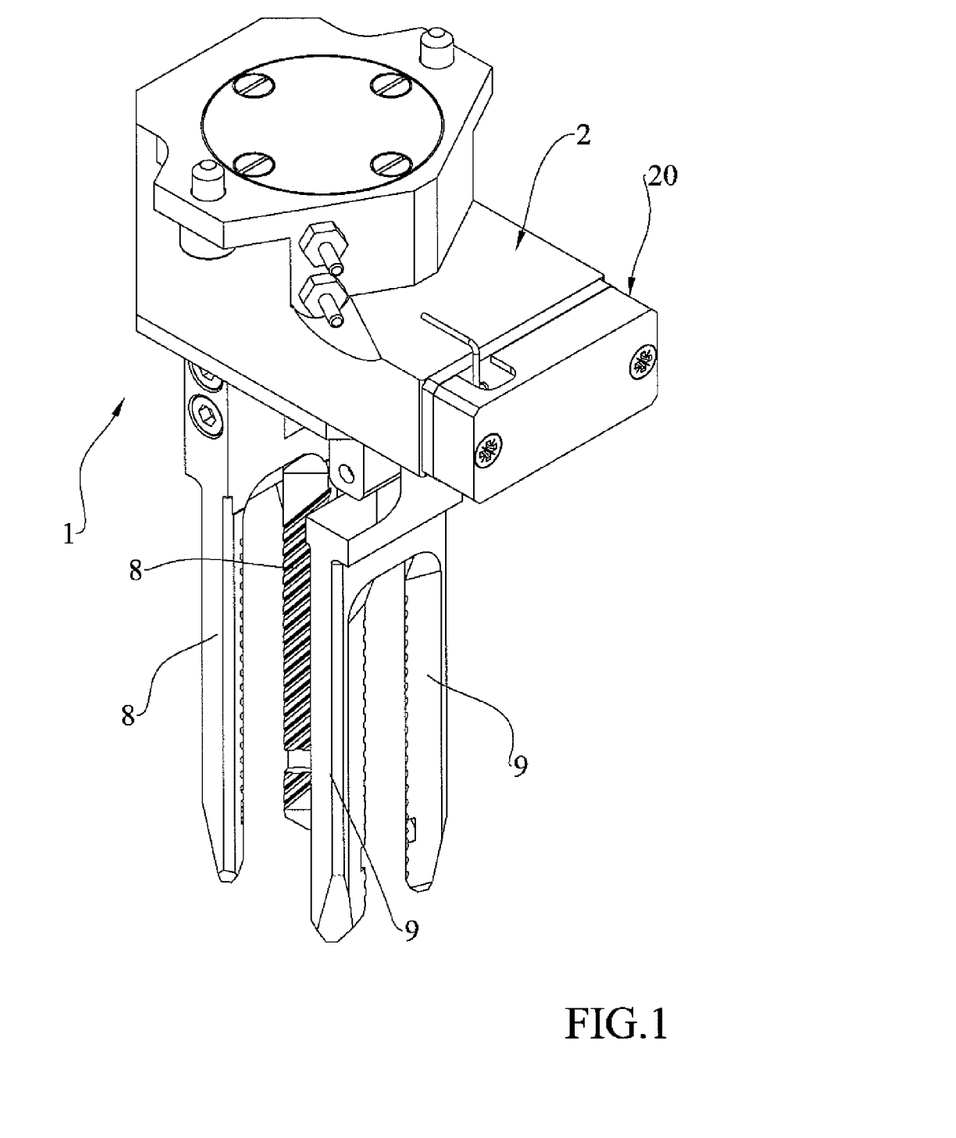
FIG. 1 is a perspective view of a container gripper provided with a gripper finger detecting sensor of Hall effect type.
Figure 2:
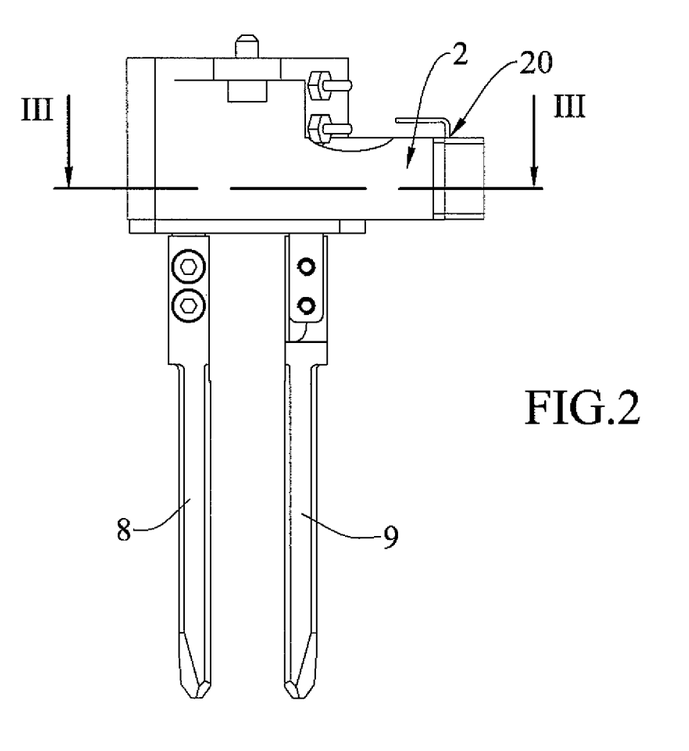
FIG. 2 is a frontal view of the container gripper with gripper fingers in open position.
Figure 3:
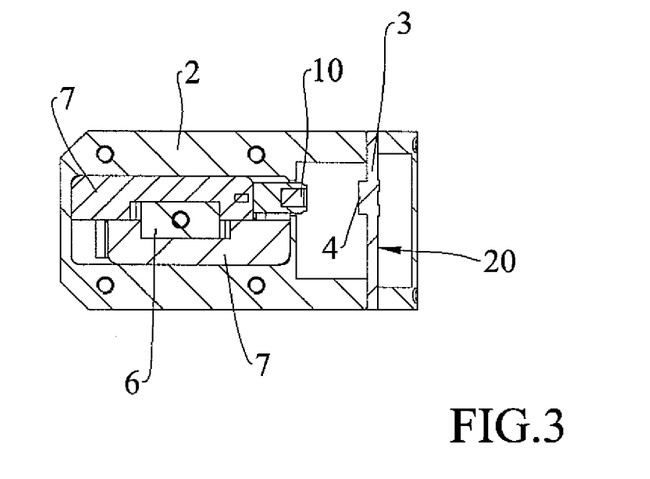
FIG. 3 is a sectional view according to line III-III of FIG. 2.
Figures 4, 5:
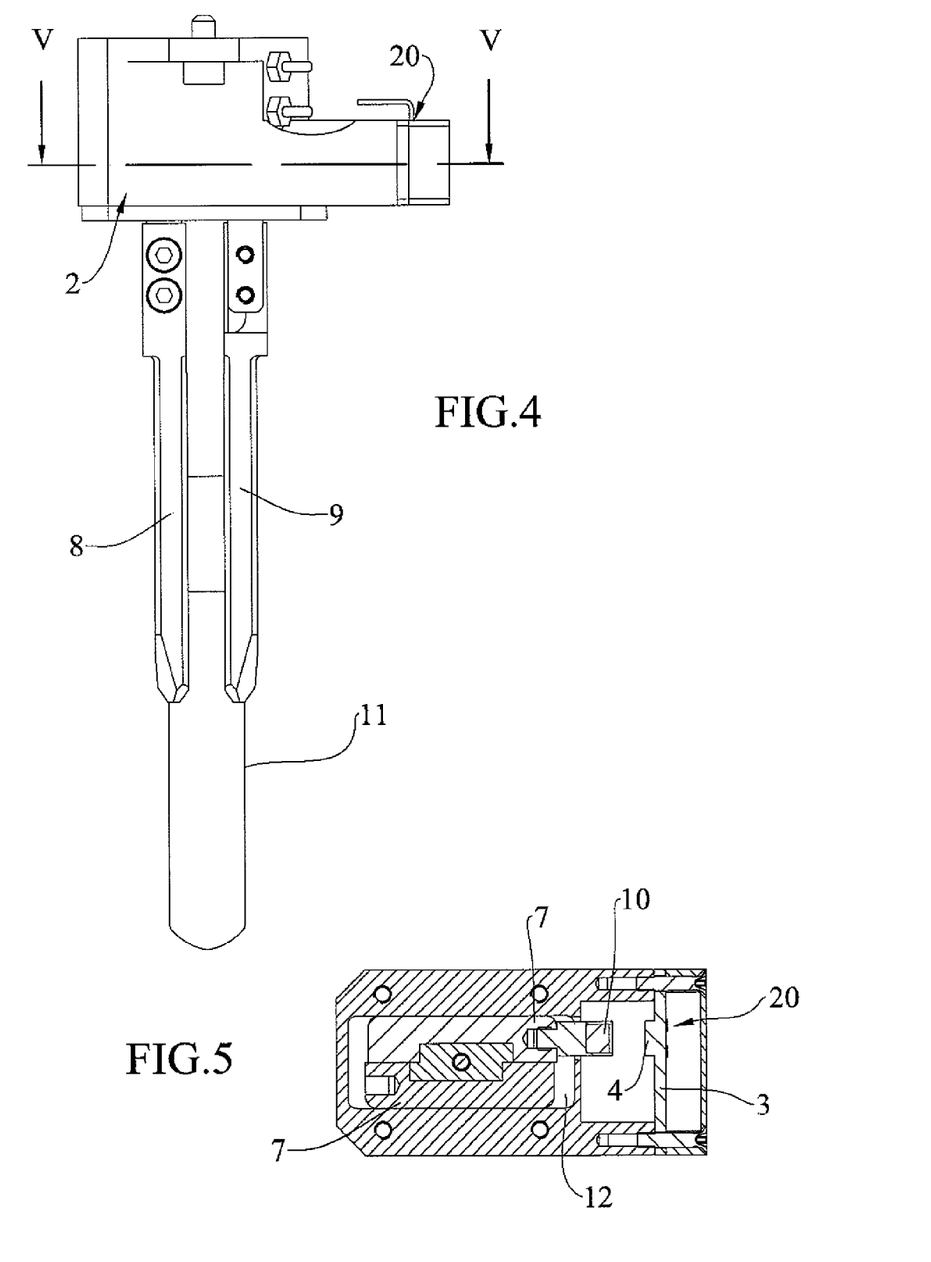
FIG. 4 is a frontal view of the container gripper with the gripper fingers in a container catch position.
FIG. 5 is a sectional view according to line V-V of FIG. 4.
Figure 6:
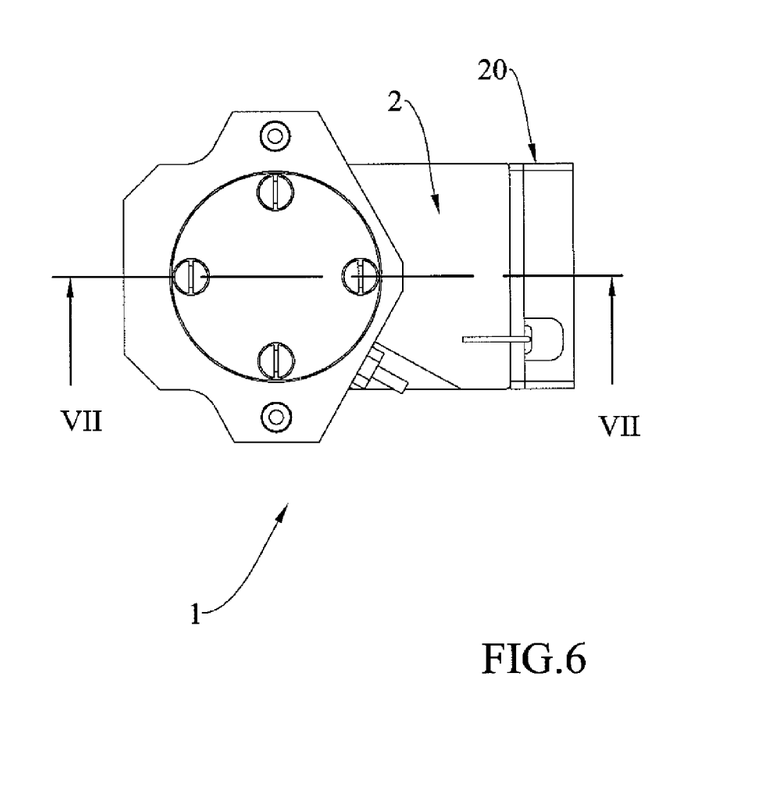
FIG. 6 is a top view of the container gripper.
Figure 7:
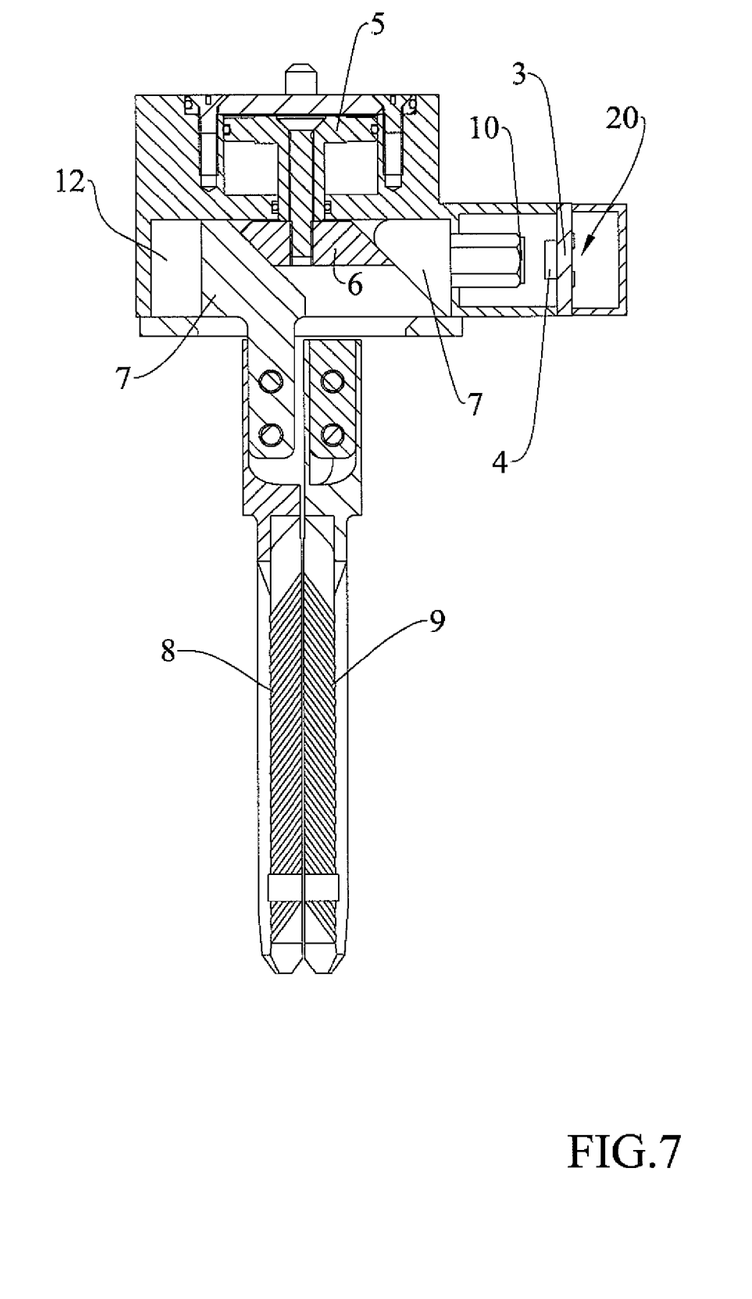
FIG. 7 is a sectional view according to line VII-VII of FIG. 6, with the gripper fingers in closed position.
Figure 8:
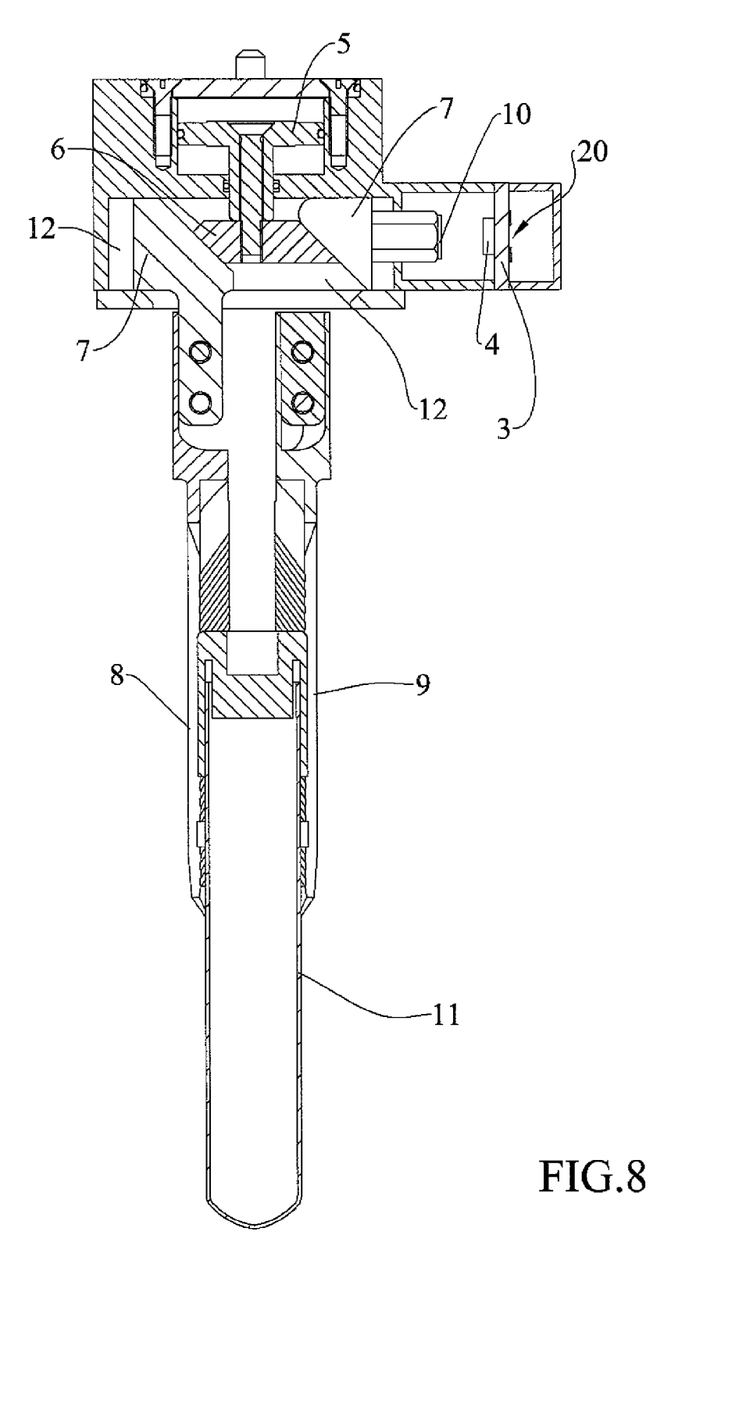
FIG. 8 is a sectional view similar to FIG. 7, with the gripper fingers in a container catch position.

A container gripper 1 comprises a main frame 2 which houses a pneumatic piston 5 (FIGS. 7-8) for actuating a wedge 6 which, by means of supporting members 7 slidingly included in an internal chamber 12, moves in a synchronous way two-by-two mounted fingers 8-9 between an open position (FIG. 2) and a closed position (FIG. 7).

Said finger supporting members 7 engage with the wedge 6 such that, if the wedge 6 goes down pushed by the piston 5, said members 7 open the fingers 8-9 due to a cam type connection between inclined walls of the wedge 6 and the supporting members 7.

Said main frame 2 supports a finger displacement detecting device 20 formed by a circuit card 3 fixed to the main frame 2 and provided with a Hall effect sensor 4, and by a magnet 10 fixed to one of two fingers supporting members 1 and therefore movable with respect to the Hall effect sensor 4 (FIGS. 3, 5, 7 and 8).

A different distance between the sensor 4 and the magnet 10 means a different magnetic field detected by the Hall effect sensor 4.

When the driven piston 5 pushes down the wedge 6 (FIG. 8), the fingers 8-9 are opened and the magnet 10 moves toward the fixed Hall effect sensor 4.

On the contrary, when the driven piston 5 moves upward together with the wedge 6 (FIG. 7), the fingers 8-9 are moved towards a closed position to grip a container and the magnet 10 moves far from the fixed Hall effect sensor 4.

When the fingers stop the closing movement against the lateral wall of a container, the Hall effect sensor 4 detects a transversal size of the gripped container and delivers an electric signal indicative of the detected transversal size or diameter.

Figure 9:
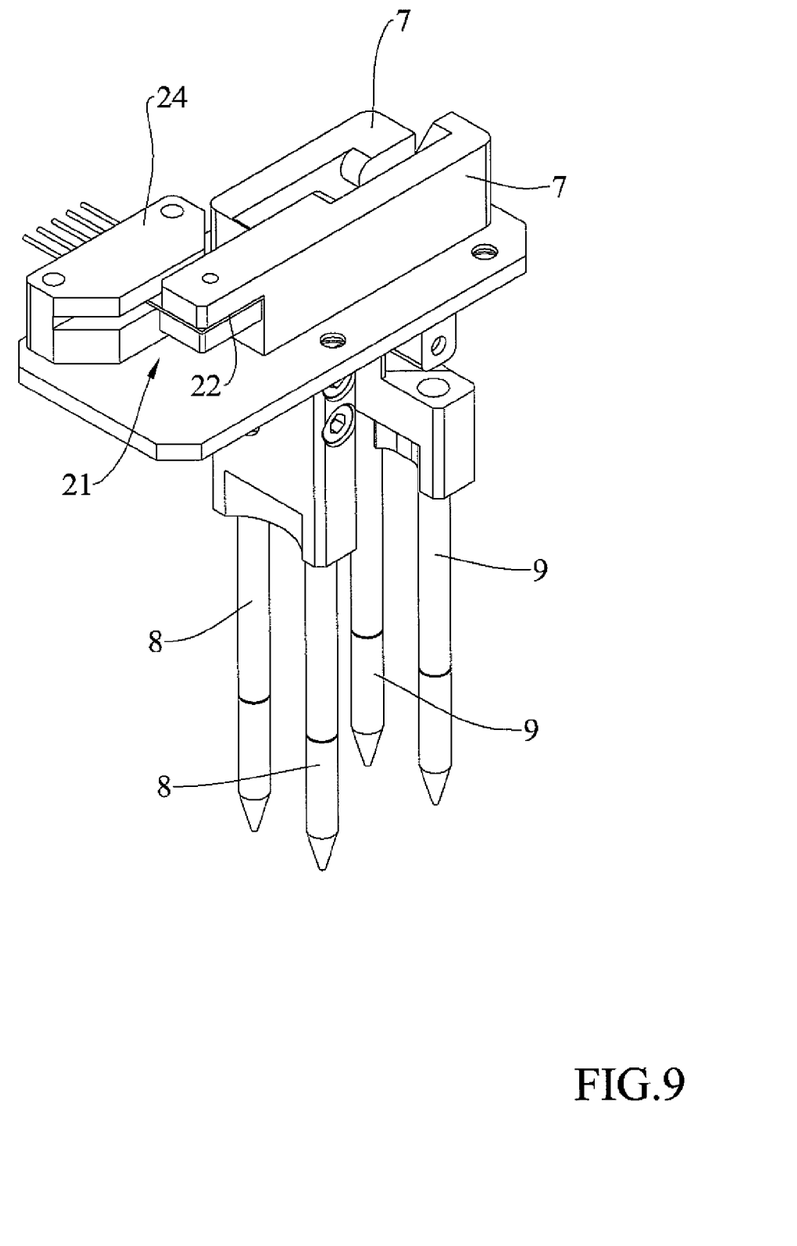
FIG. 9 is a perspective view of internal parts of a further container gripper including a finger detecting sensor consisting of a linear optical encoder.
Figure 10:
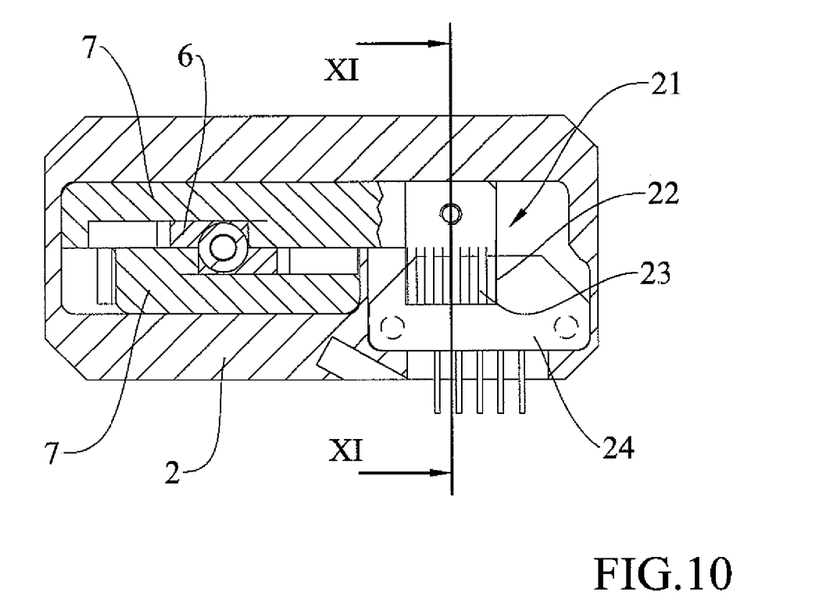
FIG. 10 is a sectional view similar to FIG. 5 which is concerned with the gripper-sensor assembly of FIG. 9.
Figure 11:
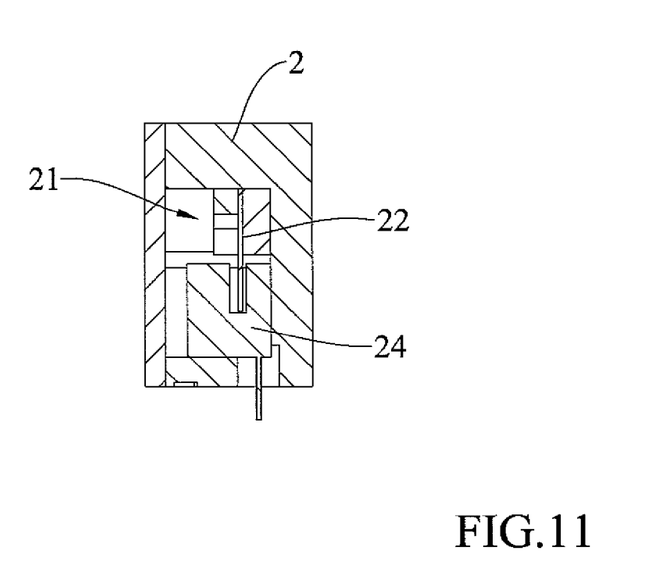
FIG. 11 is a sectional view taken along line XI-XI of FIG. 10.

The detecting device 20 formed by the magnet 10 and the Hall effect sensor 4 may be replaced by an optical encoder 21 formed by a flat card or optical ruler 22 fixed to one of the finger supporting members 7 and provided with a number of parallel optical lines 23 and by a C-shaped optical counter 24 capable of counting the number of lines 23 passing through the optical counter responsively to the transversal size of the gripped container.

The invention claimed is:

1. A container gripper comprising a main frame containing movable supporting members, which are operative for moving gripper fingers between an open position and a closed position, and a finger displacement detecting sensor fixed to the main frame and positioned to be responsive to the instantaneous position of the gripper fingers, wherein said main frame houses a pneumatic piston for actuating a wedge which slidingly engages the movable supporting members for moving the gripper fingers by a cam-type connection between inclined walls of the supporting members and the interposed wedge, whereby the gripper fingers are moved in a synchronous way between an open position and a closed position, and a magnet fixed to one of the movable supporting members and positioned opposite to the finger displacement detecting sensor and movable in a bipolar head-on mode toward and away from the finger displacement detecting sensor, wherein the movement between the magnet and the finger displacement detecting sensor is in the same direction as that of the supporting member.

2. The container gripper according to claim 1, wherein said wedge is movable between a raised position, in which the fingers are closed, and a lowered position, in which the fingers are open.

3. The container gripper according to claim 1, which comprises four fingers, two by two, fixed to synchronously movable supporting members.

4. The container gripper of claim 1, wherein the finger displacement detecting sensor is a Hall effect sensor.

5. A container gripper for gripping a container which comprises:

a main frame containing movable supporting members disposed therein, gripper fingers operatively connected to the movable supporting members and extending from the main frame, means for moving the movable supporting members which, in turn, move the gripper fingers in a synchronous way between an open position and a closed position, a finger displacement detecting sensor fixed to the main frame and positioned to be responsive to the instantaneous position of the gripper fingers, and a magnet fixed to one of the movable supporting members and positioned opposite to the finger displacement detecting sensor and movable in a bipolar head-on mode toward and away from the finger displacement detecting sensor, for establishing a variable magnetic field therebetween, wherein the finger displacement detecting sensor is responsive to the instantaneous position of the gripper fingers.

6. The container gripper of claim 5, wherein the container is a test tube.

* * * * *